Figure 1:
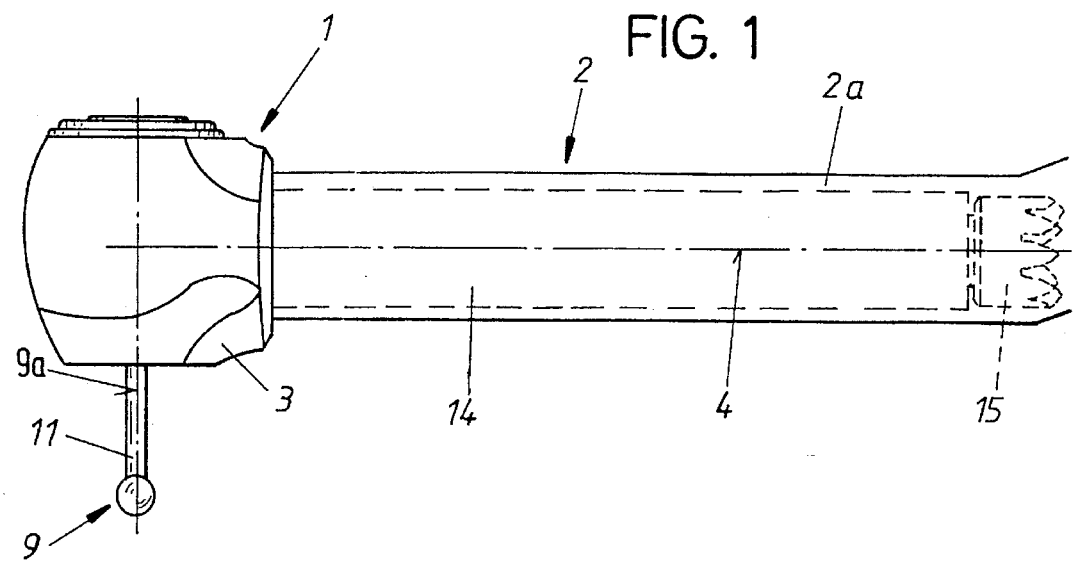

United States Patent [19]

Loge

[11] Patent Number: 5,584,689
[45] Date of Patent: Dec. 17, 1996

[54] ANGLED OR STRAIGHT HANDPIECE WITH A RELEASABLE MOUNTING DEVICE FOR A TOOL, IN PARTICULAR FOR MEDICAL PURPOSES

[75] Inventor: Hans Loge, Biberach, Germany

[73] Assignee: Kaltenbach & Voigt GmbH & Co., Biberach, Germany

[21] Appl. No.: 282,973

[22] Filed: Jul. 29, 1994

[30] Foreign Application Priority Data

Jul. 30, 1993 [DE] Germany .......................... 43 25 665.1
Mar. 14, 1994 [DE] Germany .......................... 44 08 574.5

[51] Int. Cl.[6] ........................................................ A61C 1/14
[52] U.S. Cl. ........................................... 433/128; 433/127
[58] Field of Search ............................... 433/126, 127, 433/128

[56] References Cited

U.S. PATENT DOCUMENTS

| 2,010,210 | 8/1935 | Witt | 433/128 X |
| 4,007,528 | 2/1977 | Shea et al. | 433/128 |
| 4,940,410 | 7/1990 | Apap et al. | 433/128 X |
| 5,028,181 | 7/1991 | Jenkins et al. | 433/128 X |

FOREIGN PATENT DOCUMENTS

| 2822708 | 12/1978 | Germany . |
| 3012152 | 10/1981 | Germany . |
| 3012240 | 10/1981 | Germany . |
| 3029284 | 11/1983 | Germany . |
| 3442386 | 6/1985 | Germany . |
| 3040537 | 2/1986 | Germany . |
| 4218683 | 12/1993 | Germany . |
| WO90/00885 | 2/1990 | WIPO . |

*Primary Examiner*—Nicholas D. Lucchesi
*Attorney, Agent, or Firm*—Scully, Scott, Murphy & Presser

[57] ABSTRACT

In a handpiece (2) having a housing (3), a drive sleeve (7) mounted therein, into which drive sleeve a tool (9) can be inserted with its shaft (11) and which drive sleeve is mounted in the housing to be rotatable around its middle axis (9a) by a drive, a releasable coupling for rotational locking connection of the shaft (11) in the drive sleeve (7), and a releasable coupling for axial connection of the shaft (11) with the drive sleeve (7), whereby each coupling is formed by a coupling recess (18) in the shaft (7) and a coupling pin (19) on the drive sleeve (7) engaging in the coupling recess, the two couplings are formed by at least one common coupling recess (18) and the common coupling pin (19) is mounted to be moveable between a coupling position engaging in the coupling recess (18) and a decoupling position releasing the coupling recess (18) and is biased into its coupling position and against the shaft (11) by the force of a spring (34).

26 Claims, 6 Drawing Sheets

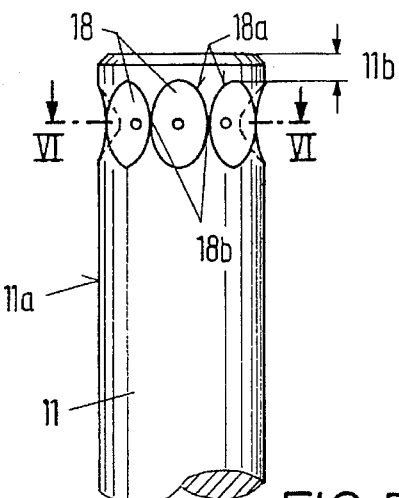
FIG. 5
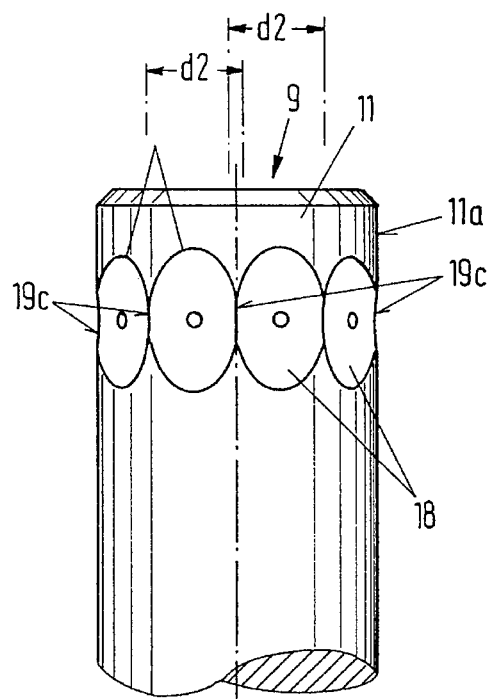
FIG. 7
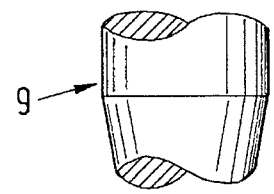
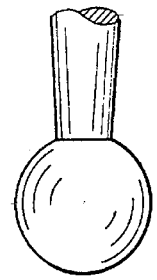
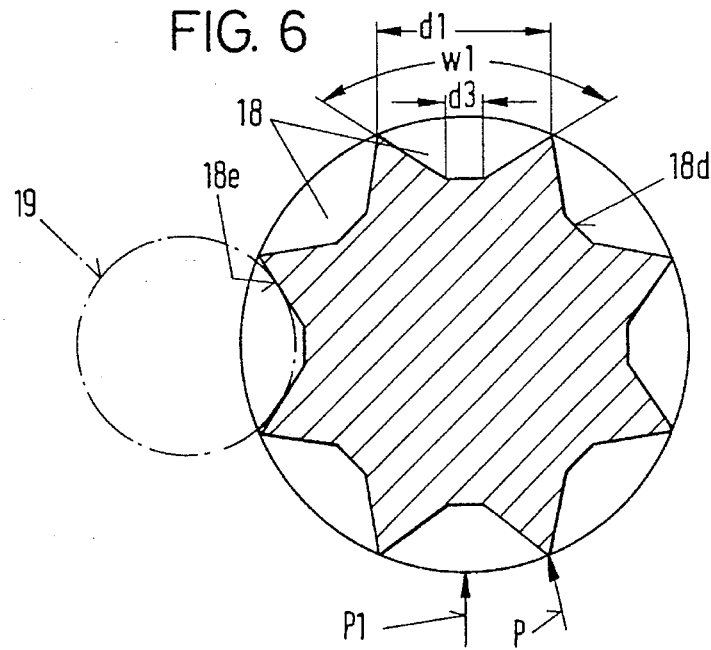
FIG. 6

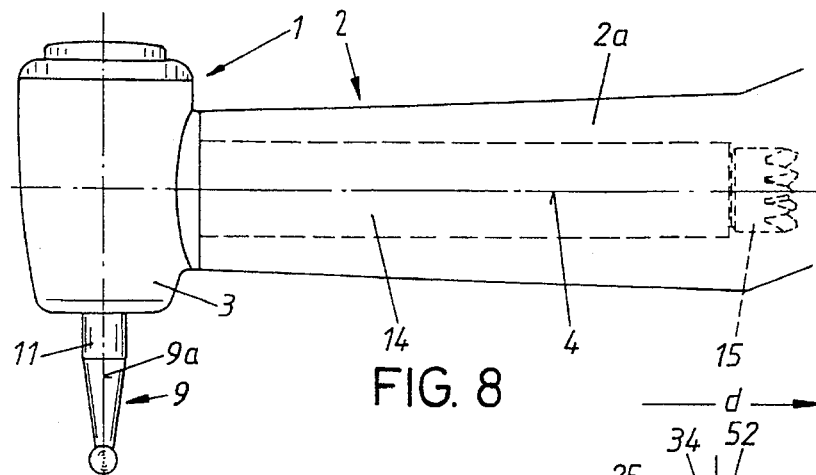
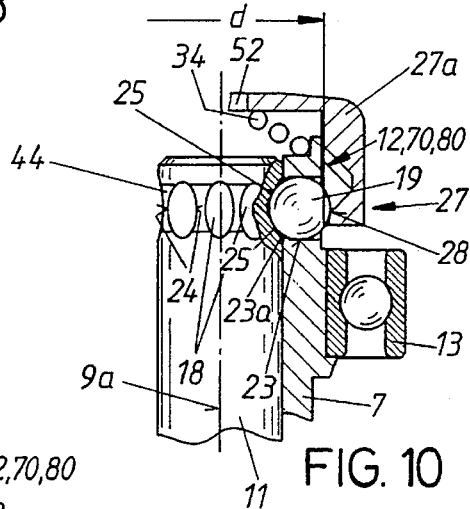
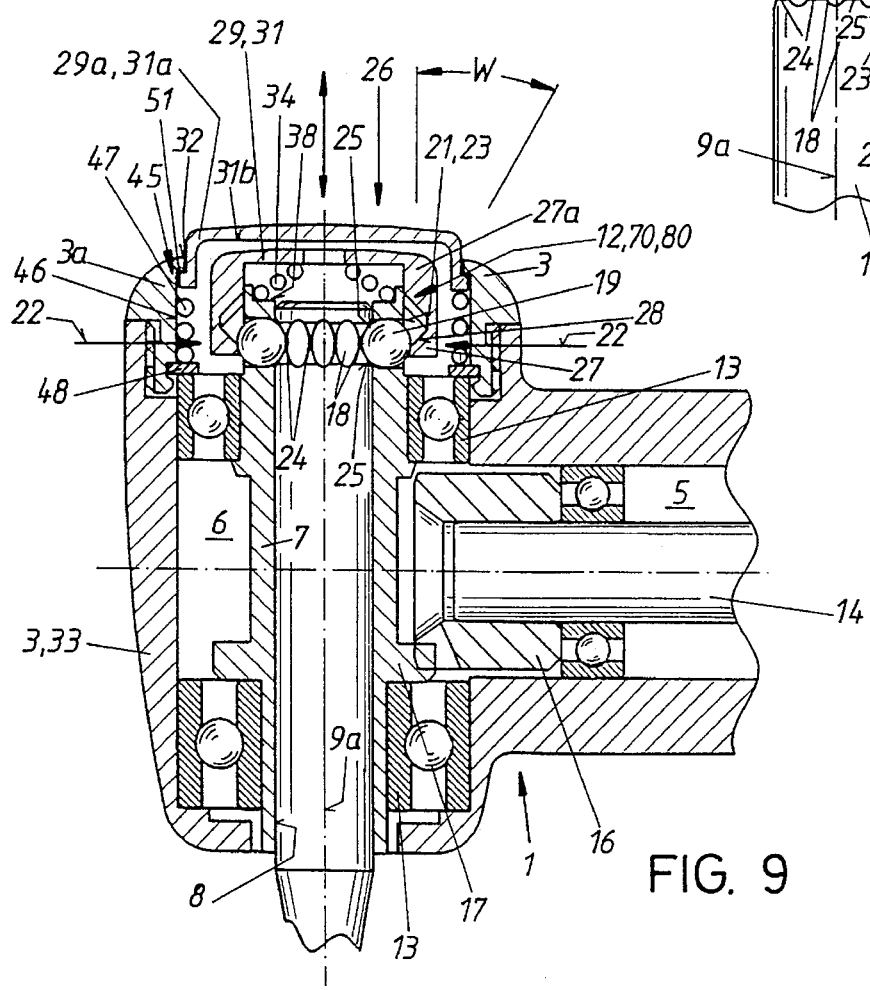

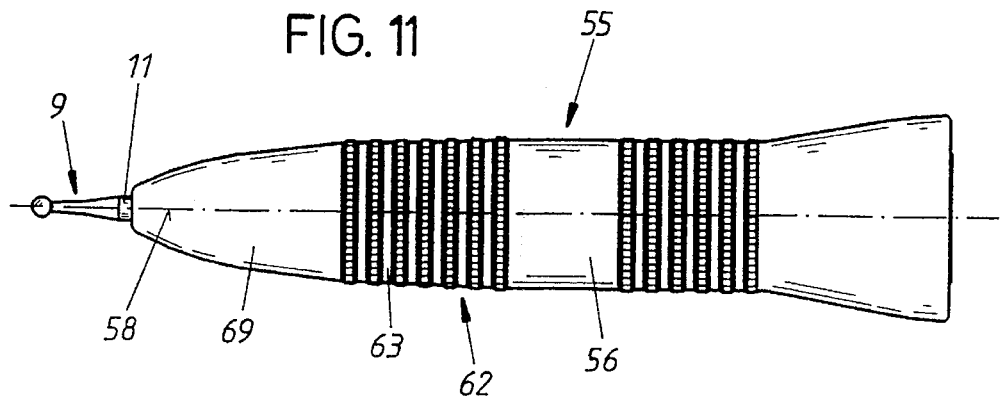
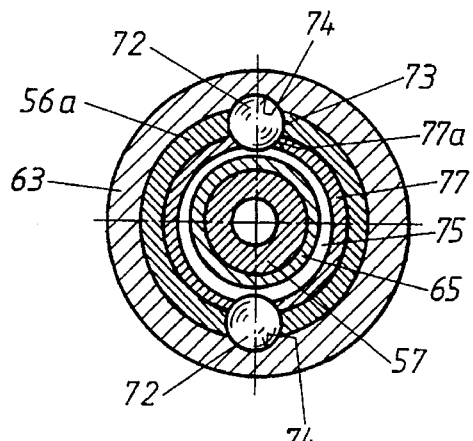
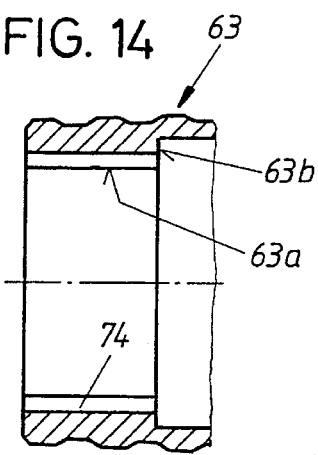
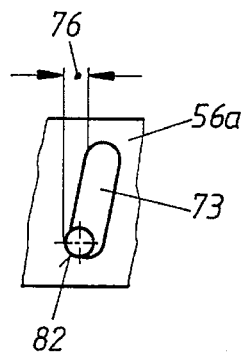
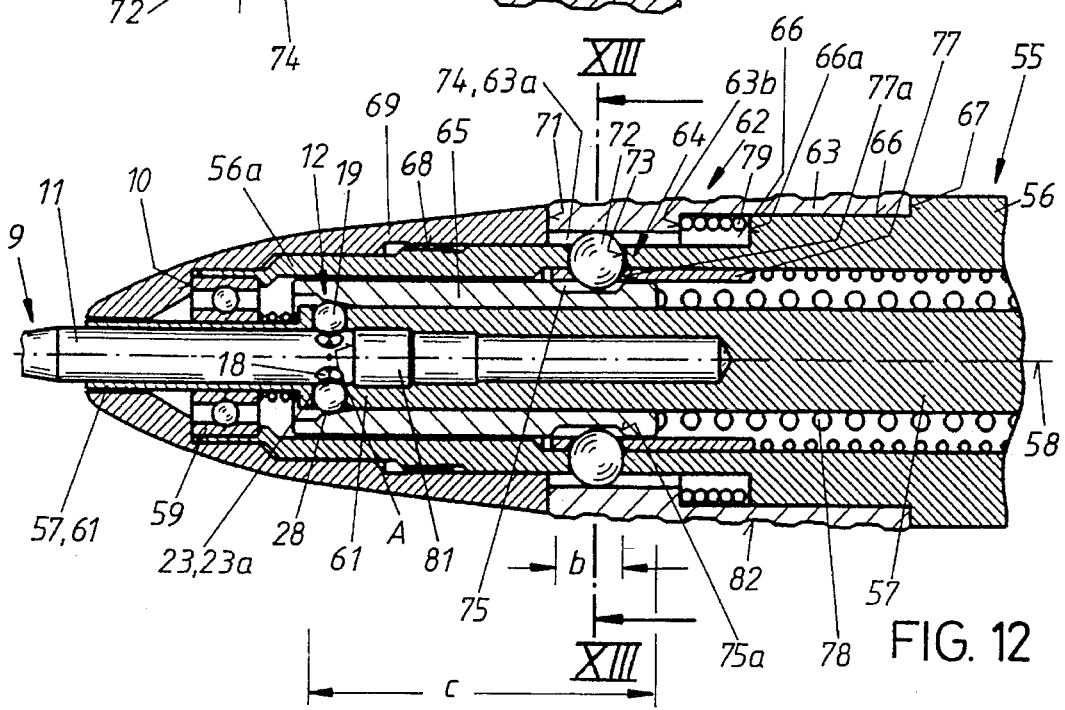

ANGLED OR STRAIGHT HANDPIECE WITH A RELEASABLE MOUNTING DEVICE FOR A TOOL, IN PARTICULAR FOR MEDICAL PURPOSES

The invention relates to an angled or straight handpiece according to the preamble of claim 1, 2, 3, 4 or 5.

Such a handpiece may be, inter alia, a medical or dental treatment instrument or a handpiece for a medical or dental laboratory.

Medical or dental treatment instruments differ from one another inter alia in terms of the functions of the tools which they carry or in terms of the function of the drive. There are treatment instruments of which the tool, for a treatment process, is set into rotation by the drive present, in order to carry out various functions. One function consists in the material detaching removal of tooth material, as is the case e.g. with drilling, machining or grinding of a tooth.

Such a treatment instrument with a rotationally driven tool can also be used, with appropriate formation of the tool, to transmit a rotational drive force to rotatable parts, e.g. to tighten or loosen screws present at the treatment location. For such a function, the tool is normally driven at a low speed of rotation, e.g. 1 to 3 rpm. In contrast, the tool is driven at a higher rate of rotation, such as e.g. up to 40 000 rpm and higher, for a material detaching work procedure.

With other kinds of medical and dental treatment instruments, the tool is moved axially to and fro, as is the case e.g. with tooth files or treatment instruments for root canals. Also, treatment instruments have already become known with which the tool is both displaced to and fro in its longitudinal direction and simultaneously rotated around its longitudinal axis or swung to and fro.

In the use of a medical or dental treatment instrument, the treatment tool must frequently be replaced or exchanged, e.g. when it is worn out or is to be replaced by a different treatment tool. Two couplings serve for the releasable attachment of the treatment tool in the treatment instrument, namely one coupling for rotational locked connection of the shaft in the drive sleeve and one coupling for axial connection of the shaft in the drive sleeve. In each case one of the two couplings serves for the drive of the tool, whilst the other coupling serves for the retention of the tool in the drive sleeve and prevents an unintended removal from the drive sleeve. If the tool shaft is inadequately retained in the drive sleeve there is a danger of the tool being released during the treatment, which can have serious consequences at the treatment location.

Since the measures for releasing or mounting or exchanging a tool on the one hand interrupt the treatment of the patient and on the other hand demand the attention of the person carrying out the treatment, many devices have already been developed which are intended to simplify the mounting and release of the treatment tool in the treatment instrument.

For this purpose, known devices have a recess in the shaft formed by means of a flattening of the shaft, with which recess there is associated a coupling pin in the drive sleeve which takes the shaft. In order to achieve a fastening of the shaft in the drive sleeve which is as free from play as possible, a rather exact matching between the base of the coupling recess and the end face of the coupling pin bearing on the base is necessary. However, the attainment of such an exact matching makes more difficult the introduction of the coupling pin into the drive sleeve, since introduction is possible only in the exact matching position. Devices with such a coupling for rotational locking connection of the shaft in the drive sleeve are described for rotationally driven treatment tools in DE-A-28 22 708, DE-B-30 12 152, DE-A-30 12 240, DE B 30 40 537 and DE-A-34 42 386.

In DE-A-28 22 708 there is described a dental treatment instrument in the form of an angled head, which has, along with the above-described coupling for rotational locking connection of the shaft in the drive sleeve, a coupling independent thereof for axially connecting the shaft in the drive sleeve. The latter coupling has two mutually radially opposed roller-like coupling pins, which are mounted each in a recess of the drive sleeve, are biased radially inwardly by a spring and latch into a circumferential groove in the shaft of the tool for coupling the tool. Thereby, it is ensured by the circumferential groove that the tool can be inserted in any rotational disposition, the coupling pins being radially outwardly displaced and springing self-actingly into the circumferential groove in their coupling position. To release the tool a spike can be inserted through a hole in the housing from the side away from the tool, with which spike the tool can be pushed out, the coupling pins being displaced radially outwardly out of the circumferential groove against the spring force acting on them.

There is described in DE-A-34 42 386 a dental treatment instrument with a so-called angled head in which the treatment tool in the form of a drill is likewise rotatably mounted. The treatment tool is fixed in the circumferential direction by means of a releasable coupling for rotationally locked connection—in the form of a flattened recess on the shaft of the tool and a coupling projection or pin engaging in the recess, and is fixed by a releasable coupling for axial connection with the drive sleeve—in the form of a latch member which is biased radially inwardly into a circumferential groove of the shaft by means of a ring spring and which can be radially outwardly removed from the circumferential groove by means of a pressure member on the side of the angled head away from the tool, in order to be able to remove the tool from the drive sleeve.

A rotational locking function between the treatment tool and a drive associated with the tool exists both with such treatment instrument in which the treatment tool is driven rotationally and with such treatment instruments in which the treatment tool is displaced by the drive to and fro in its longitudinal direction and possibly also simultaneously in the circumferential direction.

Figure 4:
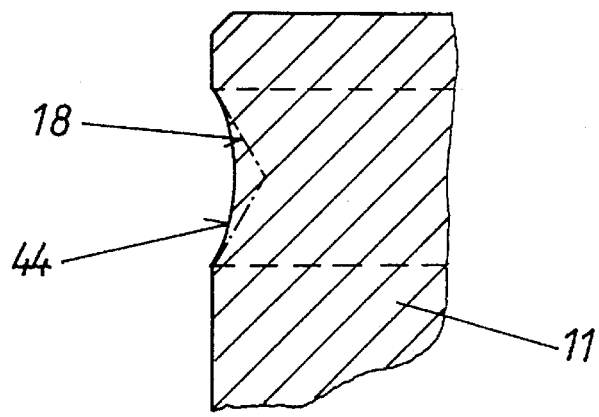

There is described in WO 90/00884 a treatment instrument in the form of an angled head with a treatment tool which is displaced exclusively to and fro in its longitudinal direction, the treatment tool being a tool file the shaft of which is mounted either by means of a drive sleeve which is axially displaceable to and fro (FIG. 2) or is mounted directly in the angled head (FIG. 4). In the first-mentioned case, a releasable coupling for axial connection of the tool shaft with the drive sleeve is provided by a clamp connection not represented in detail. A releasable coupling for rotational locked connection between the shaft and the drive sleeve is not needed because the drive sleeve is not rotated.

Further, with this known treatment instrument, an angular position setting device is provided between the treatment tool and the drive sleeve, which is formed by a coupling pin arranged on the shaft and projecting radially and axially which pin can in each case be axially inserted into one of several coupling recesses arranged on the end face of the drive sleeve distributed around the circumference, when the tool is inserted. Such an angular position setting device is important in particular for such treatment tools with which the tool has a non-round in particular blade-form cross section, as is the case with a tooth file.

Further, a rotation prevention coupling is effective between the drive sleeve and the angled head housing, which coupling is formed by a longitudinal guide between the drive sleeve and the angled head housing in the form of a coupling pin projecting radially inwardly from the angled head housing which pin engages in a longitudinal groove arranged on the outer circumference of the drive sleeve.

Furthermore, with these known treatment instruments an excessive rotation protection coupling is associated with the treatment tool, which coupling releases the rotational fixing of the tool when a torque is effective at the tool which exceeds a predetermined value. This excessive rotation protection coupling is formed in that the longitudinal groove on the housing which receives the coupling pin is arranged in a flange of the drive sleeve (FIG. 1) or of the tool shaft (FIG. 4) which is made of such a soft material that this coupling can be overcome under the effect of an excessive torque on the tool—which clearly involves crushing and damage to the material of the flange.

There is described in D-A-42 18 683 a dental treatment instrument with a treatment tool which can be displaced in its longitudinal direction, in which there are provided between the housing and the drive sleeve a rotation prevention coupling, an excessive rotation protection coupling and an angular position setting device, there being furthermore between the drive sleeve and the tool shaft a releasable coupling for rotational locking of the shaft in the drive sleeve and a releasable coupling for axially connecting the shaft in the drive sleeve, formed by a clamping connection between the shaft and the drive sleeve. In this known configuration, the excessive rotation protection coupling and the angular position setting device are formed by two mutually engaging toothed parts between the drive sleeve and the housing, of which one tooth part can be pressed in the axial direction of the tool out of the toothed connection in order to release the excessive rotation protection coupling or to set a particular angular position. In the engaged position of the toothed parts, the rotation prevention coupling is effective.

All the above-described known configurations have the common disadvantage that the insertion and fastening of the tool involves a considerable manipulative effort which demands great attention from the user. This is inevitable because the tool must be inserted into the treatment instrument in such a disposition that the rotational locations of the associated coupling recesses match the coupling pins. Even if markings were to be provided for this purpose, indicating this particular position of the treatment tool, manipulative effort and attention are necessary since first the markings must be attended to and then also the placement of the treatment tool must be attended to.

In all known cases, even when markings should be present, the tool shaft is first inserted into the treatment instrument, then rotated to a greater or lesser degree until the positions of the coupling recess and the coupling pin agree, and then pushed further in into the coupling position.

When there are available several coupling possibilities of an angular position setting device, arranged distributed around the periphery, as described in WO 90/00885, the necessary manipulative effort and the necessary attention is less but nonetheless required.

A handpiece of the kind considered here is also used, preferably in a straight configuration, for a medical, in particular dental laboratory, in which material detaching work is carried out in particular on artificial body parts or models by means of a tool having a rotational function which can be mounted in the handpiece. The handpiece is suitable for transmitting a relatively large working effort to the tool and differing tools can be mounted or released or exchanged in a user-friendly manner and quickly. A handpiece of the kind described is offered on the market by the assignee under the designation K9-handpiece type 950, and is thus known. In this handpiece the holding of the tool, both in the axial and in the circumferential direction, is based on the clamping tension of a slit conical clamping sleeve.

The object of the invention is to provide a medical or dental treatment instrument of the kind indicated in the introduction such that whilst requiring little manipulative effort, a secure tool mounting and/or holding and/or positioning is achieved.

This object is achieved by the features of claim 1, 2, 3, 4 or 5.

The solution provided by the invention in accordance with claim 1 has the advantage that only one common releasable coupling is provided, both for rotation locking connection and for axial locking connection, whereby the radially moveable coupling pin latches self-actingly into the coupling recess and presses elastically against the shaft so that a firm and secure tool mounting is achieved. The arrangement is such that the coupling pin, biased by the spring force preferably radially inwardly, is pressed radially outwardly by the inserted tool shaft and latches self-actingly in the coupling recess in so far as this recess is aligned with the coupling pin. However, the tool can also be put into place in a user-friendly manner when the shaft is inserted up to its insertion end position in such a disposition, rotated in the circumferential direction, in which the disposition of the coupling recess does not match the disposition of the coupling pin. In this case, all that is needed is a rotation of the tool until the coupling pin self-actingly latches into the coupling recess. A further axial insertion of the tool, such as is then needed in the prior art when the coupling recess does not match the coupling pin, is not necessary with the configuration in accordance with the invention.

For the radial introduction of the coupling pin into the coupling recess a preferably ring-like control element can also be provided, having—relative to the bias axis—a divergent control contour or control surface, which control element is displaceable in particular elastically by means of a spring and presses the coupling pin into the coupling recess.

The object of the invention is also achieved by claims 2, 3, 4 or 5 which relate to medical or dental treatment instruments of particular configurations and to different couplings. With regard to the advantages which can be achieved by these solutions according to the invention, attention is directed to the advantages already described above, for the purpose of avoiding repetition. With regard to all solutions in accordance with the invention, and in particular with regard to the solutions contained in claims 4 and 5, it is to be noted that upon overloading of the tool the tool is self-actingly deactivated, whereby damage neither to the tool nor to the associated coupling need be feared. The coupling spring force and the control surfaces or edges present are to be appropriately dimensioned or formed. It is, moreover, significant that a coupling in accordance with the invention having a coupling recess in the shaft of the tool and a coupling pin engaging yieldingly therein is capable of forming all couplings in accordance with the invention and therefore provides for a significant reduction of the outlay for construction and manufacture and also of the necessary manufacturing area.

Within the scope of the invention the term coupling pin is to be understood very broadly, since many forms of configuration are capable of fulfilling the function. A coupling element, e.g. a pin or peg-like coupling element, convex towards the coupling recess is involved, which can thus be introduced into the coupling recess.

The radial outward movement of the coupling pin into its ready-for-coupling position upon insertion of the tool shaft can be achieved in that the coupling pin is provided with a abutting slope or a rounding at the side at which the tool shaft makes contact, by means of which slope or rounding the coupling pin is pressed radially outwardly upon contacting of the tool shaft.

Various configurations can be provided in the invention for releasing the coupling. There can be provided a mechanism, e.g. a lever mechanism, which carries the preferably radially moveable coupling pin out of the coupling recess. It is also possible to reduce or remove the biasing of the coupling pin, e.g. in that the support for a coupling spring is moved radially away.

Thereby it is further of advantage to form the coupling pin wedge-shaped or rounded, in particular hemispherically shaped, at its end towards the coupling recess in the axial direction of the tool and/or in the circumferential direction. By these means several advantages are achieved. On the one hand the coupling pin latches better into the coupling recess. On the other hand it is possible to displace the coupling pin out of the coupling recess with the application of a certain force by turning the tool, and thus to release the coupling. Further, such a configuration makes possible a self-acting centering of the tool in the coupling position, whereby the attachment is further simplified.

It should be noted that for a coupling in accordance with the invention for the rotational locking connection and for the axial locking connection of the shaft in the drive sleeve, two flanks or edges bounding the coupling recess in the circumferential direction and one flank or edge which bounds the coupling recess on the side away from the insertion direction of the tool, are sufficient for a satisfactory functioning. The coupling pin is capable of reliably latching into such a coupling recess bounded on two sides when a stop is provided in the drive sleeve which restricts the insertion movement, which stop is effective in the position in which the coupling pin engages directly behind the last-mentioned flank or edge. Such a configuration fulfils not only the purpose of rotational locking but also that of securing the tool against unintentional falling out or unintentional removal. It is particularly advantageous to bound the coupling recess on all sides by an in particular rounded flank or edge, in particular formed by a round recess, preferably a calotte.

By means of the configurations according to the invention an overload protection coupling is in each case simultaneously provided, which allows a self-acting decoupling when there is effective at the tool an active or passive torque and/or an axial pulling or pushing force which is or are greater than a predetermined value, which is determined e.g. by the elastic limit of the tool and/or a load limit of the body to be treated. The overload protection coupling self-actingly releases the drive connection with the tool, so that the tool can freely rotate or can be displaced longitudinally without a damaging load value arising. With a rotationally driven tool, such an overload protection coupling is e.g. of advantage particularly when a rotational or turning force is transmitted with the tool, as is the case e.g. with a screwing tool. With an axially displaceable tool, the overload protection coupling is of advantage particularly when the tool has a non-round cross section. With such tools there is the danger that a torque which could lead to damage can be applied to the body to be treated, e.g. a tooth, with the treatment instrument and the tool. With such an excessive rotation protection coupling the transmittable torque is limited to a non-damaging value.

With a tool which can only be displaced longitudinally, an overload protection coupling effective in the longitudinal direction can prevent the tool from exercising a pulling or pushing force beyond a certain value on the body to be treated. By these means, the safety of the treatment is significantly improved and ensured.

Within the scope of the invention it is advantageous to provide a plurality of coupling recesses arranged distributed around the circumference and at least one or more coupling pins, in particular of the same number as the coupling recesses. By these means not only can the coupling force or tension be increased but also the ease of insertion and mounting of the tool shaft. It is thereby particularly advantageous to provide the coupling recesses in such a number and/or size that the neighbouring recess edges of two coupling recesses neighbouring each other in the circumferential direction lie closely next to one another or end at a common recess peripheral edge. By these means it is achieved that, in virtually any insertion disposition, the tool shaft self-actingly latches into one of the two neighbouring coupling recesses upon simultaneous lateral swinging.

In the case that a plurality of coupling recesses are arranged distributed around the circumference, the configurations according to the invention simultaneously form also an angular position setting device for the tool which makes it possible to introduce the tool into the drive sleeve in different angular positions. Thereby it is also possible to displace the tool from one angular position to another by turning through or overcoming the coupling.

Although there is known from EP 0 305 357 a treatment instrument for an endodontic filing tool the shaft of which is held with its free end region by means of a releasable coupling which is formed by a plurality of calottes in the outer surface of the shaft, distributed around the circumference, and two coupling balls which sit in radial bores of a tool holder and engage in the calottes in the coupling position, this instrument is however a treatment instrument from a different technical field, the filing tool of which is secured against rotational and against axial movement. For holding the filing tool, a bush-like fixed tool holder is provided in the bush walls of which the bores with the coupling balls are arranged. Moreover, the arrangement is such that in the coupling position the coupling balls engage into the calottes without biasing and furthermore a slight play must be present between the coupling balls and the calottes so that the filing tool can carry out radially directed vibration movements. A cylindrical tensioning sleeve serves for holding the coupling balls in the their coupling positions which sleeve is longitudinally displaceable for coupling and releasing and the cylindrical internal surface of which bounds the coupling balls radially outwardly.

The solutions according to the invention are thus suitable for tools which are rotationally driven, longitudinally displaced or also driven in a manner combining these two drive directions. Thereby, the solutions according to the invention is based not only on a coupling effective in a form-locking manner, as is the case with the state of the art, but upon the combination of a form-locking and a force-locking effective coupling, whereby the form-locking is provided by the engagement of the coupling pin in the coupling recess and the force-locking is provided by the biasing with which the coupling pin is pressed against the coupling recess.

The invention relates also to a tool in accordance with claim 23 that can be employed in particular with the handpieces in accordance with the invention and which leads to comparable advantages.

Features are contained in the subclaims which contribute to problem solving, which further simplify manipulations both for coupling and decoupling and which lead to simple constructions and small constructions, which can be advantageously integrated into a straight or angled treatment instrument or handpiece and furthermore lead to an economically manufacturable construction.

Figure 2:
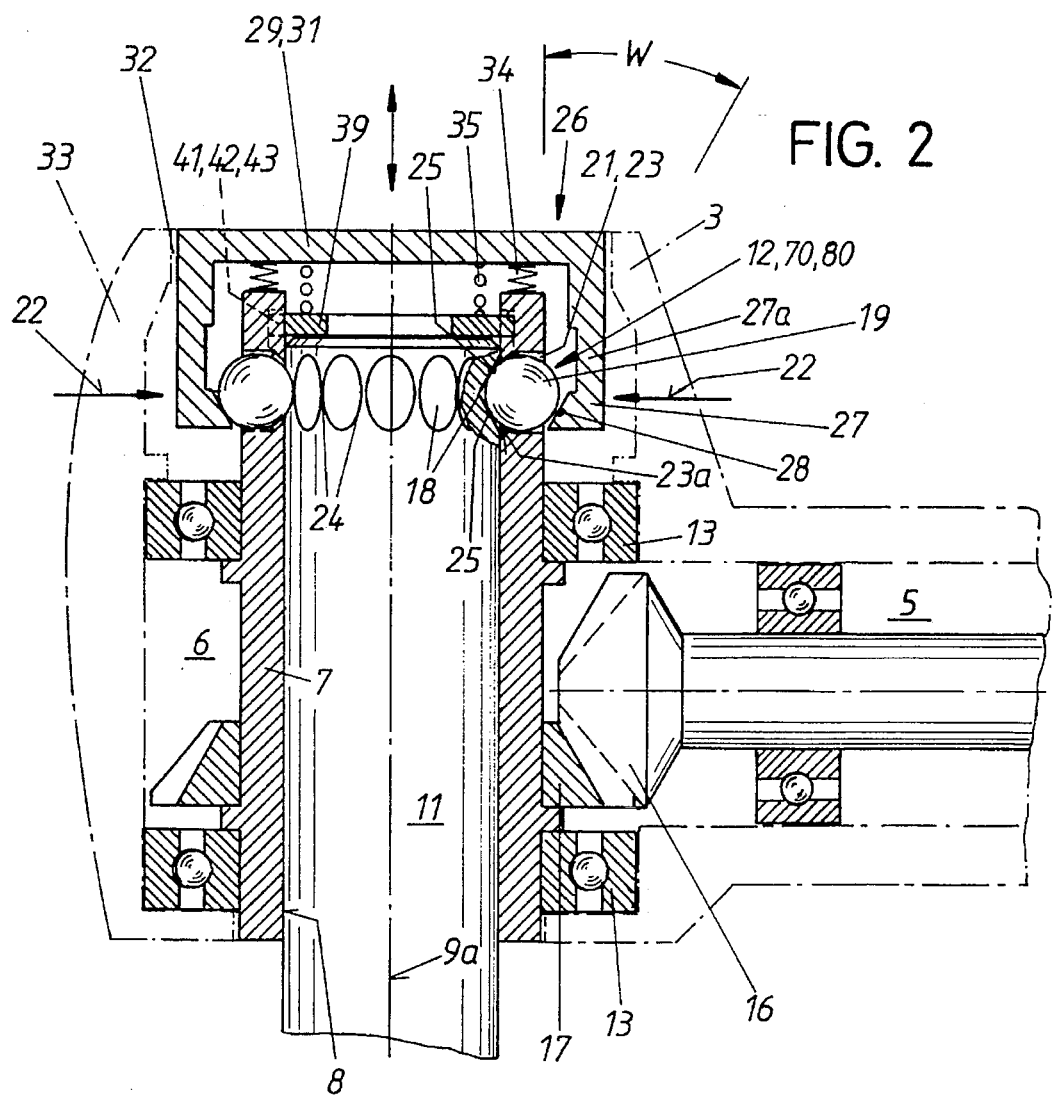
Figure 3:
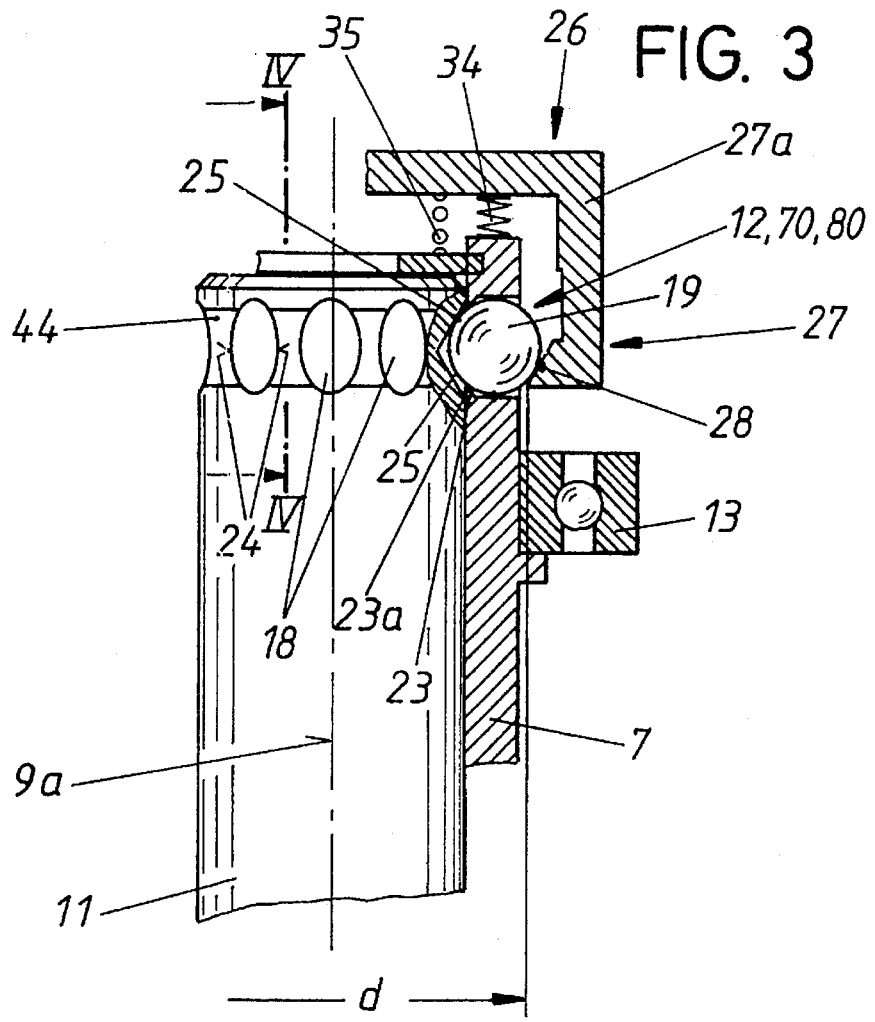
Figure 16:
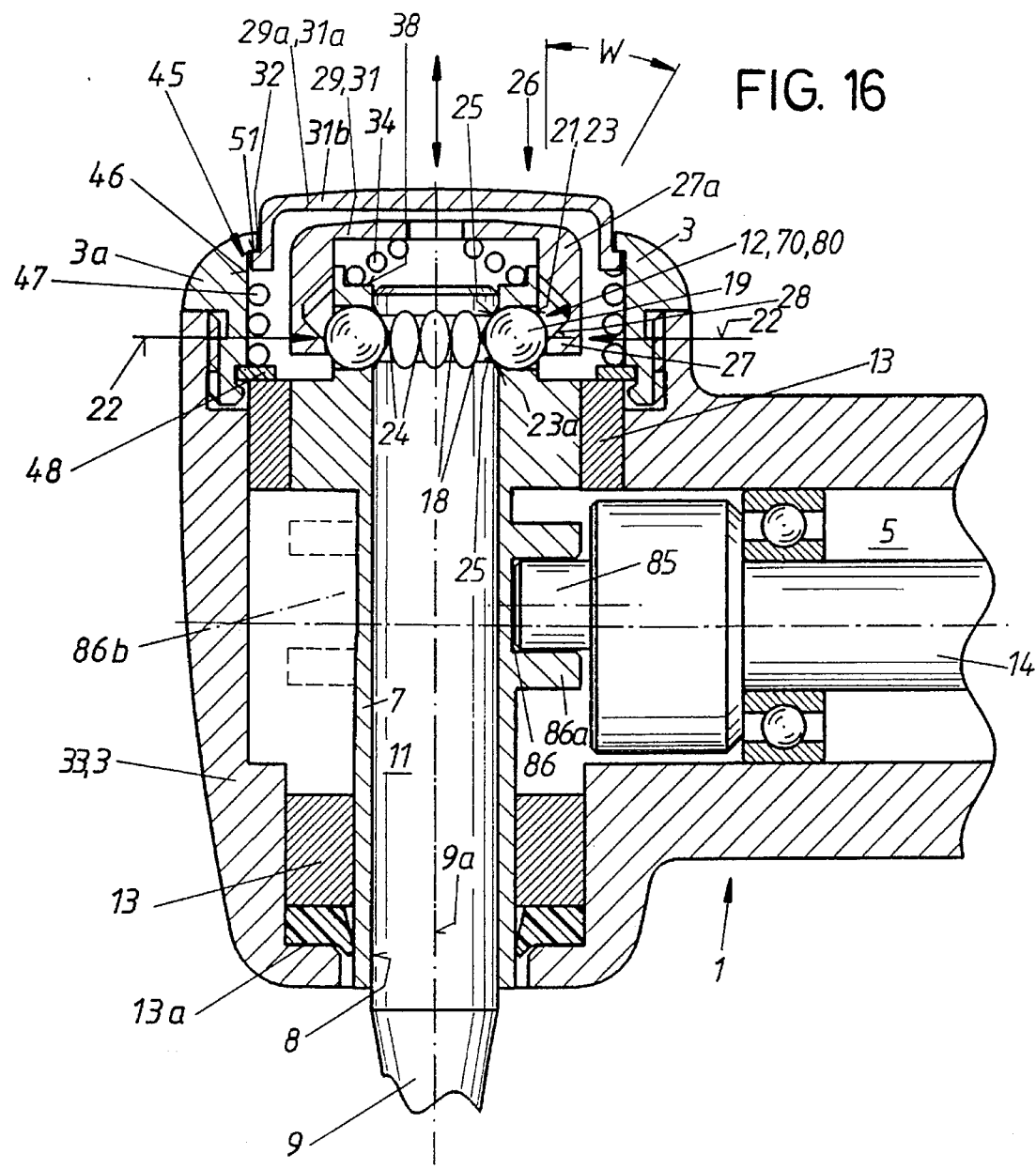

In the following, the invention and further advantages which can be attained thereby will be described in more detail with reference to preferred embodiments and simplified drawings, which show:

FIG. 1 the forward end or head end of a handpiece in accordance with the invention, in the form of a dental treatment instrument with a so-called angled head, in a side view;

FIG. 2 a longitudinal section through the head end, in a representation to an enlarged scale;

FIG. 3 a detailed view, corresponding to FIG. 2, of a modified configuration;

FIG. 4 is the partial section IV—IV of FIG. 3, shown on an enlarged scale;

FIG. 5 a material removing tool for a handpiece in accordance with the invention in a side view corresponding to the direction of view P1 in FIG. 6;

FIG. 6 the section VI—VI of FIG. 5;

FIG. 7 a modified configuration of the tool shaft, in a side view corresponding to the direction of view P in FIG. 6;

FIG. 8 the forward or head end of a handpiece in accordance with the invention in the form of a dental treatment instrument of a modified configuration, in a side view;

FIG. 9 a longitudinal section through the head end of the treatment instrument of FIG. 8;

FIG. 10 a detail of the treatment instrument of FIG. 8, in a sectional representation to an enlarged scale;

FIG. 11 a handpiece according to the invention having a straight extension, in particular for a medical or dental laboratory, in a side view;

FIG. 12 the treatment instrument of FIG. 11 in axial section;

FIG. 13 the section XIII—XIII of FIG. 12;

FIG. 14 an actuating sleeve of the treatment instrument of FIG. 12, in axial section;

FIG. 15 a detail of the treatment instrument of FIG. 12, in a representation to an enlarged scale;

FIG. 16 the forward or head end of a handpiece in accordance with the invention, in the form of a dental treatment instrument with an angled head, as a further exemplary embodiment, in a side view.

In the present embodiment the forward or head end 1 is only a part of a handpiece 2 which is only partially illustrated. The head end consists of an angled head housing 3, which may be a forward extension of a grip sleeve 2a of the handpiece 2. The longitudinal middle axis of the grip sleeve 2a is referenced with 4. The invention, still to be described, can also be realized on a straight handpiece 2, as is illustrated in FIGS. 7 and 8.

As is shown in particular by FIG. 2, the angled head housing 3 or the grip sleeve 2 has an axial bearing bore 5, which forwardly opens into a step-form through-going bearing bore 6 at right angles to the axial bearing bore, in which step-form bearing bore a substantially hollow cylindrical drive sleeve 7 is rotationally mounted. A treatment tool 9, illustrated in FIG. 1, can be inserted into the cylindrical bore 8 of the drive sleeve 7, from the tool side, with a cylindrical retaining shaft 11 arranged along the middle axis 9a of the tool and the tool can be coupled with the drive sleeve 7 by means of a coupling 12. In the configuration according to FIG. 2, a rotationally driven drilling tool is involved.

For mounting the drive sleeve 7, bearings 13, which may be roller-bearings, are mounted in the housing 3 to the two sides of the longitudinal middle axis 4 with an axial spacing from one another.

For driving the drive sleeve 7, a drive shaft train is mounted in the handpiece 2, of which the forwardmost drive shaft section 14 is rotationally mounted in the mounting bore 5 and is drivingly connected with the remaining (not shown) drive shaft train by means of a toothed coupling arranged at its rearward end or a bevel gear 15 of a bevel gear drive. For the rotational drive of the drive sleeve 7, a bevel wheel is attached to the forwardmost end of the drive shaft section 14, which wheel engages with a ring-like bevelled wheel 17 which is attached to the drive sleeve 7 or is formed in one piece therewith.

The coupling 12 serves for rotational locking connection of the tool shaft 11 into the drive sleeve 7 and for axially connection, and the coupling is formed by means of at least one coupling recess 18 in the outer surface of the tool shaft and a coupling projection or pin 19 associated with the drive sleeve 7, which projection or pin is mounted in the drive sleeve 7 in a radial guide 21, moveable between a coupling position and a decoupling position, and is biased into its coupling position, i.e. in the direction of the coupling recess 18, by means of a spring force 22.

The coupling recess 18 preferably has the form of a calotte, preferably the form of an in particular approximately right angled or obtuse angled hollow cone, and in the present embodiment the coupling pin 19 is formed by a ball which is radially moveable in a radial bore 23 forming the guide 21. The inner edge region of the bore 23 is somewhat tapered in order to prevent the ball 19 falling out of the bore 23 inwardly, when the mounting shaft 11 is removed. When the ball 19 engages in the coupling recess 18, a small spacing is present between the ball and the taper 23a.

With its axially or circumferentially opposing edges or flanks the coupling recess 18 forms in each case a coupling element pair 24 or 25, between which the coupling pin 19 engages. By means of the coupling element pair 24, spaced apart from one another in the circumferential direction, the rotational locking of the tool shaft 11 and the drive sleeve 7 is provided, whilst by means of the coupling element pair 25, spaced apart in the longitudinal direction of the tool shaft 11, an axially effective coupling element is provided.

An actuating device 26 for releasing the coupling is associated with the coupling 12. The device comprises a pressure member 27, which is subject to the effect of the spring force 22 and urges the coupling pin 19 into its coupling position in the coupling recess 18. In the present embodiment, the pressure member 27 is mounted axially movably, but not radially movably, whereby it presses with a pressure surface 28, running obliquely with respect to tool axis 9a, against the coupling pin 19. The actuating device 26 has further a manually operable actuating element 29, in this case in the form of a push-button 31, which is preferably accessible from the side away from the treatment tool 9 and is preferably mounted so as to be displaceable to and fro along the rotational axis of the drive sleeve 7. The access to the push-button 31 is available by means of a hole 32 in the wall 33 of the housing 3 away from the treatment tool 9, whereby the push-button 31 registers approximately with the upper rim of the hole 32 in its initial position away from the tool (coupling position), or projects beyond the rim or housing to the extent of its stroke, or by somewhat more. A compression spring 34 is arranged to be effective between the push-button 31 and the drive sleeve 7, which compression spring biases the push-button 31 into its initial position away from the tool, in which position the oblique pressure surface 28 presses against the coupling pin 19 and thereby hinders a further outward movement (coupling position) of the push-button 31.

The pressure member 27 and the actuating element 29 can be arranged rotatably or non-rotatably with the drive sleeve 7.

The coupling 12 can be overcome or released, in the sense of an overload protection coupling, both in the circumferential direction and also axially, as a result of the elastic biasing of the coupling pin 19. That is, as result of a turning of the treatment tool 9 in the circumferential direction, or as the result of a displacement of the treatment tool 9 in its longitudinal direction, the coupling pin 19 can be displaced out of the coupling recess 18, and thus release the coupling, if the rotational or axial force acting on the treatment tool is correspondingly large.

The coupling 12 according to the invention thus also provides an overload protection for the treatment tool 9 which overload protection is provided in that—in the case of overload—the coupling 12 automatically or self-actingly releases.

When a coupling 12 as described above is present in a simple configuration, in order to attach the tool shaft 11 the tool shaft 11 is pushed into the drive sleeve 7, whereby attention may be directed, e.g. with the aid of predetermined markings, to the placement of the coupling recess 18 as nearly as possible in the same rotational position as the coupling pin 19. Upon pushing in, the tool shaft 11 can in one movement be inserted up to its axial end insertion position in which the coupling 12 latches and which may be limited by a stop. Insofar as the positions of the coupling recesses 18 and of the coupling pin 19 are not aligned, the tool shaft 11 is to be so far rotated in the inserted position that the coupling pin 19 self-actingly engages in the coupling recess 18.

To release the coupling 12, the push-button 31 is pressed inwardly with one finger of the operating hand, whereby the pressure member 27 distances itself from the coupling pin 19 and the coupling pin 19 is relieved. By means of further finger pressure, or by means of the force of a simultaneously effective compression spring, the tool shaft 11 can be axially pushed towards the tool side, out of the coupling engagement.

It can be of advantage to choose the angle of inclination W of the pressure surface 28 such that the tension is self-limiting or such that the coupling 12 can be overcome or released by action on the treatment tool 9 in the circumferential direction or in its longitudinal direction. In both cases the treatment tool 9 can be pushed out of the coupling engagement by manually pressing the press button 31 inwardly.

It is of advantage to arrange a plurality of coupling recesses 18 distributed around the circumference, so that when the tool shaft 11 is inserted into the drive sleeve 7 a plurality of coupling recesses 18 are available for latching with the coupling pin 19, whereby latching will be achieved more readily. Thereby, one or a plurality of coupling pins 19 arranged distributed around the circumference may be provided.

With such a configuration, as realized in the present embodiment, it is favourable to arrange the pressure member 27 on a ring arranged coaxially with the drive sleeve 7 and surrounding the coupling pins 19, which ring may be guided in a guide, e.g. on the drive sleeve 7 or in the housing 3. Thereby, one or more compression springs 34, arranged distributed around the circumference, for biasing the coupling pins 19, may be provided. Advantageously, these compression springs 23 are arranged between the end face 38 of the drive sleeve 11 that is away from the tool and the push-button 31, which push-button is preferably formed by a radial wall of the pressure ring 27a.

For the above-described ejection of the treatment tool 9 upon decoupling, a thrust member 39 may be axially displaceably mounted in the region of the end of the drive sleeve 7 remote from the tool, which thrust member stands in drive connection with the push-button 31 and upon pressing of the push-button 31 is pressed inwardly against the end of the tool shaft away from the tool, so that the tool shaft can be pushed out. It is also advantageous to arrange the compression spring 35 between the preferably ring-form thrust member 39 and the push-button 31.

Between the drive sleeve 7 and the possibly ring-form thrust member 39, a longitudinal guide 41 is preferably provided for the thrust member 39, which longitudinal guide may be formed, e.g. in that radial guide attachments 42 engage in corresponding longitudinal guide grooves 43 in the drive sleeve and are longitudinally displaceable.

It is further advantageous, in accordance with the configuration of FIGS. 3 and 4, to provide a ring groove 44 in the outer surface of the tool shaft 11, in the transverse plane of the coupling recess or coupling recesses 18, the cross-sectional form of which ring groove may be rounded in correspondence with the radius of the ball or hollow-cone shaped. Thereby it is significant that the effective depth of the ring groove 44 is less than the effective depth of the coupling recess 18, so that the coupling element pair 24, effective in the circumferential direction, and the coupling element pair 25, effective in the longitudinal direction are present.

By means of the ring groove 44 an axial fixing is provided which is effective if the coupling pin or coupling pins 19 are not latched in place. By these means there is provided a guide, directed in the circumferential direction, upon insertion or rotation of the tool shaft 11 for the purpose of finding a coupling latching disposition.

Insofar as a plurality of coupling recesses 18 are provided, it is advantageous to select the number and size of the recesses such that they have a small spacing from one another in the circumferential direction, preferably border on one another or merge one into another. By these means the finding of the coupling engagement upon insertion of the shaft 11 is much simplified since—if the coupling recess 18 and the coupling pin 19 do not immediately find one another upon insertion—only a slight rotation of the shaft is needed for latching the coupling 12.

An additional ring groove 44 provides a preliminary axial fixing of the shaft 11 in the drive sleeve 7 in any rotational disposition of the insertion end position, so that the danger of the tool 9 falling out unintentionally is avoided to the largest possible extent. The presence of the ring groove also leads to the advantage that with the already present axial fixing, the latching of the coupling 12 can be brought about by rotation of the tool 9 without there being the danger of an axial displacement of the shaft 11.

For the purpose of reducing the surface compression between the ball or balls forming the coupling pin or coupling pins 19 and the conical pressure surface 28, it is advantageous to provide oblique grooves in the pressure surface 28 which are adapted to the size and form of the balls, which grooves ensure a line-form bearing of the balls in the grooves.

The tool 9 illustrated in FIGS. 5, 6 and 12, in which the same or similar parts are provided with the same reference signs, differs from the above-described tool in that the coupling recesses 18 are so arranged that the peripheral edges 19a of coupling recesses 18 neighbouring one another in the circumferential direction merge into one another and form a common peripheral edge section 19b. This can be achieved by appropriately dimensioning the diameter d1 of the hollow cone-like coupling recesses 18 on the cylindrical outer surface 11a of the shaft 11 in the circumferential direction or by appropriately dimensioning the depths of the coupling recesses and/or by the selection of an appropriate number of coupling recesses 18. It is thereby possible within the scope of the invention to effect the configuration such that the peripheral edge sections 19b are located in the outer surface 11a, as shown in FIG. 5, or so that the peripheral edge sections 19b are located below the cylindrical outer surface 11a, i.e. they are offset radially inwardly in relation to the outer surface 11a, as shown by the configuration according to FIG. 7.

In the configuration according to FIG. 5:

$$d1 = \frac{\text{circumference } U \text{ of the shaft } 11}{\text{number of the coupling recesses } 18}.$$

In contrast, in the configuration according to FIG. 7, a diameter d2 in the circumferential direction at the cylindrical outer surface 11a, schematically represented, is:

$$d2 > \frac{\text{circumference } U \text{ of the shaft } 11}{\text{number of coupling recesses } 18}.$$

In the configuration according to FIG. 7 the peripheral edge sections 19c cut one another at a radially inwardly directed spacing from the outer surface 11a, whereby inwardly concavely rounded peripheral edge sections 19c result, as shown in FIG. 7, whereby it is to be taken into account that the view according to FIG. 7 is provided with the direction of view according to arrow P in FIG. 6 whilst the view according to FIG. 5 is provided in the direction of view according to arrow P1. The concavely rounded peripheral edge sections 19c provide a retention of the shaft 11 (pressure point) which is form-lockingly effective and elastically yielding even if the coupling pin or coupling pins 19 are located upon the peripheral edge section 19c, e.g. after insertion of the shaft 11. In contrast, in the configuration of FIG. 5, a retention is provided which is only force-lockingly effective in this shaft position, based on the frictional force of the coupling recesses.

In the present configurations, the conical angle w1 of the coupling recesses 18 is preferably about 180φ. The working of the coupling recesses 18 into the shaft 11 can be achieved in various ways. Insofar as a drill or milling tool (not shown) is employed, a flattened recess base 18d is provided in the coupling recesses 18, which base is represented as a small circle d3 and is formed by a so-called stage in the middle region of the rotating drill or milling tool.

As is the case for the above-described configurations, the associated coupling element 19 bears on the hollow cone surface 18e of the associated coupling recess 18, as is schematically illustrated in FIG. 6. Between the recess base 18d and the coupling element or coupling pin 19 there is preferably a free space.

In the coupled state of the tool 9, i.e. when the coupling pins 19 are latched into the coupling recesses 18, an axial and/or circumferentially directed pulling and/or turning force on the tool 9 is needed after operation of the actuating device 26 for releasing the coupling 12, in order to force the coupling elements or pins 19 out of the coupling recesses.

The termination of the peripheral edges 18a in common peripheral edge sections 18b is advantageous because when the coupling pins 19 are located on the peripheral edge section 18b upon insertion of the shaft 11, an unstable state arises in which it can be anticipated that the shaft 11 will be rotated in one of the two circumferential directions by the spring forces of the coupling pins 19, so that the coupling pins 19 can fall into the coupling recesses 18.

In contrast, such an unstable state is not present when a circumferential spacing is provided between the coupling recesses 18, and thus a particular rotation of the shaft in the circumferential direction is needed in the above-described insertion position in order that the coupling pins 19 can fall into the coupling recesses 18.

The coupling recesses 18 are advantageously located in the free end region of the shaft 11, as shown in the Figures.

In a preferred exemplary embodiment, in which the shaft diameter is 2.5 mm, the diameter of the balls is preferably about 1.15 mm and eight coupling recesses 18 and coupling pins 19 are provided. Thereby, the spacing 11b between the free end of the shaft 11 and the coupling recesses 18 is preferably somewhat larger than half the diameter d1. Preferably, the spacing 11b is not larger than about 3 mm, preferably about 1 mm or less than 1 mm.

The configuration of the handpiece 2 according to FIGS. 8 and 9, in which the same or similar parts are provided with the same reference signs, differs from the above-described configuration in the following details.

In the configuration according to FIG. 2, the common element formed by the pressure member 27 and the actuating elements 29 or the push-button 31 rotates with the drive sleeve 7. Although it is possible to operate the push-button 31 e.g. whilst rotation is ceasing, this may be thought uncomfortable. Thus, in the configuration according to FIGS. 8 and 9, the actuating element 29 and the push-button 31 are in each case passive elements, with a manually operable active actuating element 29a, here in the form of a push-button 31a, arranged thereabove and guided longitudinally of the middle axis 9a in the housing 3 or in a cover part 3a screwed into the housing, in a guide 45. There serves for this purpose a bore 46 in the wall 33 of the housing 3 or in the cover part 3a, the active actuating element 29a or the push-button 31a being adapted to the dimensions of this bore 46 with play for movement. The active push-button 31a is biased into its upper initial position by means of a compression spring 47 the lower end of which is supported on a securing ring 48 which bounds the upper bearing 13, in which upper initial position the push-button 31a—having a preferable cap-like form (see FIGS. 8 and 9)—bears against an inner shoulder surface 51 of the bore 46 with an outer ring attachment at the free edge of the active push-button 31, which internal shoulder surface is formed by a taper in the upper edge region of the bore 46. In this initial position a small spacing exists between the radial wall 31b of the push-button 31a and the passive actuating element 29 or the passive push-button 31, the passive push-button 31 possibly having a hole 52 in its centre.

In the configuration according to FIGS. 8 and 9, only one compression spring 34 is provided for acting on the pressure member 27 or the passive actuating element 29, which compression spring may have a conical spiral form for the purpose of reducing the structural height. In this configuration, the active actuating element 29a or the active push-button 31a is arranged separately from the rotating components, so that the active actuating element or the active push-button can be operated also during rotation or as rotation ceases for the release or detachment of the tool 9.

The biasing force and the self-limiting action with which the pressure ring 27 biases the coupling pin or coupling pins 19 radially inwards is dependent not only upon the angle of inclination W of the inclined or conical surface 28 of the pressure member 27, but alternatively is dependent upon the internal diameter d of the pressure ring 27. When this internal diameter d is only slightly smaller than an imaginary circle which surrounds the balls in their coupling position, as shown in FIGS. 3 and 7, then the curvature of the balls present in this region is effective in the manner of a slightly inclined oblique surface. Thereby, on the one hand, a large radially inwardly directed biasing force is produced, and, on the other hand, the coupling is self-limiting, i.e. it is not possible to press the coupling pin or coupling pins 19 or balls radially outwardly and to pull the pressure ring downwardly by means of a longitudinal displacement of the tool. This means that with such a configuration no overload protection coupling is available which opens self-actingly upon overloading of the tool in the circumferential direction or in its axial direction.

In the configuration according to FIGS. 11 to 15, the invention is realized in a treatment instrument in the form of a straight handpiece 55. Such a treatment instrument is used in particular for dental treatments outside the oral cavity and for working on models of teeth and teeth parts in a so-called technical work station.

The main parts of this handpiece 55 are a sleeve-like housing 56 in which a drive shaft 57 is approximately coaxially arranged and mounted around a longitudinal middle axis 58 by means of a bearing 59 of which only the forward bearing is illustrated—as a roller bearing—in FIG. 12. The forward region of the drive shaft 57 is preferably formed in one piece as drive sleeve 61 for the tool 9 which can be inserted from the front into the drive sleeve 61, the forward bearing 59 sitting on the possibly partially tapered drive sleeve 61. For releasable fixing of the tool shaft 11, there is provided between the tool shaft 11 and the drive sleeve 61 a releasable coupling for rotational locking connection of the tool shaft and the drive sleeve and for axially connecting the tool shaft 11 in the drive sleeve 61, which coupling corresponds in principle to the above-described coupling 12 and is therefore provided with the same reference sign. A different actuating device 62 is provided with the handpiece 55 for releasing the coupling 12. The actuating device 62 has a rotation sleeve 63 arranged at the circumference of the housing 56 at a spacing from the forward end of the housing, which rotation sleeve is connected by a drive 64 with a pressure member 65 which, with an inclined or conical surface 28, coupling pins 19, guide holes 23 or 23a and coupling recesses 18, works against the coupling pins 19 in a manner comparable in principle with the above-described embodiment, and which therefore will not be described in more detail in this respect for the avoidance of repetition.

The rotation sleeve 63 is arranged in a forwardly stepwise tapered ring recess 66 between the rearward boundary surface 67 of the ring recess 66 and a cap 69 which can be screwed from the front onto the forward tapered section of the housing 56 by means of a thread 68, the rear surface of which cap bounds the ring recess 66 as forward limiting surface 71. The arrangement is such that when the cap 69 bears on a shoulder 72 of the tapered housing part 56a, the rotation sleeve 63 is mounted between the bounding surfaces 67, 71 with play for movement. The cap 69 is conically tapered towards its forward end.

The drive 64 converts a rotational movement of the rotation sleeve 63 into an axial movement of the pressure member 65 and has one or more, in this case two, drive pins or preferably drive balls 72 arranged distributed around a partial circle, which drive pins or drive balls are each arranged in a guide groove 73 in the tapered housing body 56a which groove runs obliquely in the circumferential direction, the diameter of the drive balls 72 being larger than the wall thickness of the sleeve-like housing body 56a. The drive balls 72 thus project beyond the wall of the housing body 56a, inwardly and outwardly, a longitudinal groove 74 being arranged in the internal surface of the rotation sleeve 63 and a circumferential groove 75 being arranged in the external surface of the sleeve-like pressure member 65, for receiving the projecting ball sections. The longitudinal groove 74 extends preferably continuously through an internal ring attachment 63a and is longer than the axial offset 76 of the inclined guide groove 73. The width b of the circumferential groove 75 is larger than the associated ball dimension, whereby the rearward boundary surface 75a of the circumferential groove 75 has a small spacing from the coupling ball or coupling balls 72 in the coupling position illustrated in FIG. 12.

Since the sleeve-like pressure member 65 forms a rotatable unit with the drive axis 57, contacting of the drive balls 72 with the pressure member 65, in the coupled condition, should be prevented. In this respect, the guide groove 73 may be tapered in the region of its lower edges, as has been described in the case of the guide bores 23 of the above-described embodiment, so that plunging of the drive balls 72 against the pressure member 65 is prevented. Preferably, a spacing sleeve 77 is fixedly inserted or held in the region of the guide groove 73 in the housing body 56a, which spacing sleeve has a guide groove 77a congruent with the guide groove 73, but which is somewhat tapered in its width, so that the drive balls 72 cannot plunge radially inwardly and have a spacing from the pressure member 65.

In the following, the functioning of the actuating device 62 will be described. In the coupling position of the coupling 12 illustrated in FIG. 12, the sleeve-like pressure member 65, whose length c is so great that its rearward end region projects into the region of the rotation sleeve 63, is biased against the coupling balls 19 by means of a compression spring 78, so that the coupling balls are pressed radially inwardly into the coupling recesses 18. For decoupling, the rotation sleeve 63 is to be rotated relative to the housing 56, against a spring force applied by means of a rotation spring 79 preferably formed by a spiral spring, which is arranged between the rear surface 63b of the ring attachment 63a and the stepped surface 66a of the ring recess 66 and which is connected at its one end with the rotation sleeve 63 and at its other end with the housing body 56a, e.g by means of angled ends which are hooked into associated holes.

The drive balls 72 are rotated with the relative rotation between rotation sleeve 63 and the housing 56, whereby the drive balls—because of the oblique running of the guide grooves 73—simultaneously move axially rearwardly, press against the boundary surface 75a of the circumferential groove 75 and thereby displace the sleeve-like pressure member 65 rearwardly against the force of the compression spring 78, so that the coupling balls 18 can be displaced outwardly by a pulling out of the tool 9, whereby the coupling 12 is released.

Because of the tension of the rotation spring 78, the rotation sleeve 63 is returned, after its release, self-actingly into its initial position and at the same time the pressure member 65 is also pushed forward into the coupling position by means of the pressure spring 78. For inserting the tool 9 into the drive sleeve 61 it is possible, with an appropriately large inclination of the oblique surface or hollow conical surface of the pressure member 65, to displace the sleeve-like pressure member 65 rearwardly against the force of the pressure spring 78, by means of the radially outward displacement of the coupling balls 19 upon insertion of the tool shaft 11, so that the tool shaft can be inserted further between the coupling balls 19 and then, when the coupling balls reach the region of the coupling recesses 18, the coupling 12 self-actingly closes because of the force of the pressure spring 78, and the coupling balls 19 latch into the coupling recesses 18 against the tool shaft 11.

With an appropriately large angle of inclination W, this coupling 12 also forms an overload protection coupling 70 effective axially and/or in the circumferential direction, which self-actingly releases upon overloading of the tool in the circumferential direction and/or axial direction.

If, however, the inclination of the oblique or hollow conical surface is less, then it is necessary to displace the sleeve-like pressure member 65 into its rearward decoupling position by means of a rotation of the rotation sleeve 63, to introduce the tool shaft in this position, and then to release the rotation sleeve 63, whereafter it is self-actingly returned into its initial position because of the spring forces or to rotate the rotation sleeve back into its initial position, whereby the coupling 12 closes self-actingly.

The configuration according to the invention having a plurality of coupling recesses 18 forms also a rotational position setting device 80 for the tool 9, which makes possible the setting of particular initial rotational positions and e.g. is of significance when a slowly rotating drive is provided, as is e.g provided for a screw turning drive in the case in which the tool is a screwdriver.

In order to ensure that the coupling recess 18 lies opposite the coupling bores 19 in the inserted position of the tool shaft 11, it is advantageous to provide a stop for the free end of the tool shaft 11 in the drive sleeve 61, which stop determines this position. Such a stop A can be formed e.g. by a stopper body 81 fixedly mounted in the drive sleeve 61.

To provide pressure points or latch positions in each of which the rotation sleeve 63 stays in place, lateral latching recesses 82 can be provided at the beginning and/or end of the guide groove 73, in which recesses the drive balls 72 latch as a result of the tension of the compression spring 78.

To increase security of gripping it is advantageous to arrange corrugations or gripping grooves 82 on the outer surface of the rotation sleeve 63.

The exemplary embodiment according to FIG. 16, in which the same or similar parts are provided with the same reference signs, shows a treatment instrument with a so-called angled head, whereby the tool 9 is driven by the drive displaceably to and fro in its longitudinal direction and is possibly also rotationally or swingably driven. Such a configuration is suitable for a tool moveable in its longitudinal direction e.g. a file or a root canal treatment tool, which are known per se.

In this configuration, the drive sleeve 7 is longitudinally displaceably mounted to both sides of the drive shaft 14 likewise in bearings 13, which may be slide bearings. A sealing ring 13a, preferably with a sealing lip is provided as a wiping ring at the tool side of the associated bearing 13, which wiping ring is effective between the housing 3 and the drive sleeve 7. The drive shaft 14 is connected with the drive sleeve 7 by a drive, in particular an eccentric drive, which transforms the rotational movement of the drive shaft 14 into a longitudinal movement of the drive sleeve 7. For this purpose, an eccentric drive pin 85 is provided on the drive shaft 14, which drive pin engages in a recess 86 on the drive sleeve 7, with play for movement, such that the drive sleeve 7 is driven in the sense of a longitudinally directed to and fro movement when the drive shaft 14 rotates. The recess 86 may be arranged directly in the drive sleeve 7 or in a lateral attachment 86a of the drive sleeve 7. If the recess 86 is closed on all sides in the plane of rotation of the drive pin 85, simultaneously with its to and fro movement the drive sleeve 7 carries out a swinging movement around its middle axis 9a. If, on the other hand, the recess 76 is formed in the manner of a circumferential groove 86b e.g in a ring attachment—which is schematically shown in a simplified manner by broken lines—the drive sleeve 7 is freely rotatable around its middle axis 9a as it is being driven, so that the drive sleeve is not fixed with regard to a particular rotational position. With such a configuration, a torque can hardly be applied with the tool 9 to the treatment location, or only a slight torque can be applied.

With this configuration also, the coupling 12 provides an advantageous connection which is effective in the circumferential direction and/or in the longitudinal direction of the tool, and/or is a rotation or angular position setting device 80 and/or an overload protection coupling 70 effective in the longitudinal direction and/or in the circumferential direction of the tool 9.

The overload protection coupling 70 is of significance in particular when the cross-sectional form of the tool is not round, as is particularly the case with a flat file of elongate cross sectional form or a flat file. In such a case, a torque can be applied to a tooth (e.g. in a tooth space) with the tool, with which the tooth could be overloaded. This is prevented by the overload protection coupling, since it prevents the transmission of a damaging torque.

The magnitude of the coupling forces can be predetermined in all exemplary embodiments by means of a predetermined tension of the spring 34 or 78.

The tool mounting device or releasable coupling device according to the invention, having at least one coupling recess 18 in the tool shaft, is suitable both for small constructional forms, in particular for dental treatment instruments, and for more powerful treatment instruments of larger constructional form, in particular for treatment handpieces for medical or dental laboratories, whereby a secure tool mounting and the transmission of larger torques is ensured. Thereby the device according to the invention is suitable, with a dental treatment instrument, for tool shaft diameters from about 1.5 mm to about 3 mm, in particular for the diameters usual in dental practices of 1.6 mm and 2.35 mm.

The configuration according to the invention is suitable both for tools 9 of metal, in particular of steel, and also plastics, whereby the tool may be either a rotational tool or a tool displaceable axially to and fro.

In the following, still further advantages which can be achieved by the invention will be described.

The mounting procedure, both with angled and also straight instruments, is user-friendly, comfortable, of easy action and, at the same time, secure.

The tool mounting makes possible a large retention force and is sufficiently robust to transmit larger torques if this is required for special instruments.

Better truth of rotation and lesser radial play of the tool.

Playless axial fixing of the tool in the instrument or handpiece.

Mounting of the tool without the need to attend to a particular angular position.

Self-acting location of the latch locking position upon mounting of the tool.

Operation with one hand is possible given the availability of an appropriate drill stand.

One compression spring of relatively small spring force is sufficient in the instrument or handpiece, which is of advantage for the quality of running.

Insensitivity of the coupling or mounting device in relation to treatment in a disinfection device, in particular a thermal disinfection device.

It is made possible that only one tool shaft configuration is needed for both straight and angled handpieces or instruments.

A stop A for the tool 9, in accordance with FIG. 12, can also be provided in all other configurations according to FIGS. 1 to 10 and 16. Since a stop A restricts the insertion movement, it can make unnecessary the flank sections 18*e* on the tool or the edges of the at least one coupling recess 18.

When the flank sections 18*e* are present on the tool or edges are present, it is advantageous to provide a small spacing between the stop A and the tool shaft 11 in the (latched) coupling position, so that upon insertion of the shaft 11 the stop A prevents an insertion far beyond the coupling position and determines a rough coupling position, and a centring in the coupling position is achieved self-actingly as a result of the spring force.

Insofar as the coupling 12 provides an axially effective overload protection coupling, it is however to be noted that the stop A cancels the effectiveness of the overload protection coupling in one axial direction, namely in the axial direction of the stop.

I claim:

1. A handpiece (2, 55) having a releasable mounting device, said device holding a medical tool (9), said handpiece including a housing (3, 56), a drive sleeve (7, 61) mounted in said housing (3, 56) for rotation about a center axis by a drive (9*a*, 58) so as to be axially non-displaceable, said tool (9) being insertable with a shaft (11) thereof; a releasable coupling for rotational locking connection of the shaft (11) with the drive sleeve (7), said tool shaft being engaged by said drive sleeve and being restrained from any radial movement said releasable couplings being formed by a plurality of identical coupling recesses (18) in the shaft (11) evenly distributed around the circumference thereof and by coupling pins (19) on the drive sleeve (7, 61) engaging in said coupling recesses, said coupling pins (19) being mounted so as to be radially moveable in radial guides (21) of the drive sleeve (7), a movement stop (23*a*) being associated with respectively each said coupling pin (19), said stop preventing the coupling pins (19) from falling out of the drive sleeve (7) upon the tool (9) being withdrawn, the radial dimensions of the coupling pins (19) being larger than the radial thickness of the drive sleeve (7, 56*a*), said coupling pins (19) in the coupling position of the couplings each being biased into the coupling recesses (18) radially inwardly by an axially displaceably mounted pressure ring, said ring axially acting with an inner conical surface (28) against the outer ends of all coupling pins (19) and being acted upon axially by the force of the spring, the pressure ring (27) being manually accessible or by an actuating element (29, 29*a*) from outside the housing (3) and being axially displaceable against the force of the spring (34, 78) into a release position releasing the coupling pins (19).

2. A handpiece (2, 55) having a releasable mounting device, said device holding a medical tool (9), said handpiece including a housing (3), a drive sleeve (7) mounted in said housing so as to be reciprocably displaceable in the longitudinal direction of a center axis (9*a*) and being selectively non-rotatable, rotatable and swingable about the center axis by a drive, said tool (9) being insertable with a shaft (11) thereof into said sleeve, a releasable coupling for axial connection of the shaft (11) with the drive sleeve (7), said tool shaft being engaged by said drive sleeve and being restrained from any radial movement and a further releasable coupling for connection of the shaft (11) with the drive sleeve (7) in a circumferential direction, said couplings being formed by at least one coupling recess (18) in the shaft (11) and at least one coupling pin (19), said pin being moveably mounted between a coupling position engaging in the coupling recess (18) and an uncoupling position releasing the coupling recess (18) in a radial guide (21) of the drive sleeve (7) and being biased into its coupling position by the force of a spring (34), a movement stop (23*a*) being associated with the coupling pin (19) which prevents the coupling pin (19) from falling out of the drive sleeve (7) when the tool (9) is withdrawn, and a mechanism which is manually accessible from the outside for shifting the coupling pin from the coupling recess (18) into the uncoupling position thereof.

3. A handpiece (2, 55) having a releasable mounting device, said device holding a medical tool (9), including a housing (3), a drive sleeve (7) mounted in said housing and which is mounted so as to be reciprocably displaceable in the longitudinal direction of a center axis (9*a*) and being selectively non-rotatable, rotatable and swingable around the center axis (9*a*) by a drive, which is selectively mounted to be rotatable around the center axis (9*a*, 58) by a drive and axially non-displaceable in the housing (3, 56), and into which the tool (9) can be inserted with a shaft (11) thereof; a releasable coupling for the axial connection of the shaft (11) with the drive sleeve (7), said tool shaft being engaged by said drive sleeve and being restrained from any radial movement and a further releasable coupling for connection of the shaft (11) with the drive sleeve (7) in the circumferential direction, an overload protection coupling (70) being arranged between the drive sleeve and the shaft (11), all of said couplings being formed by at least one coupling recess (18) in the shaft (11), at least one coupling pin (19), which is moveably mounted between a coupling position engaging the coupling recess and an uncoupling position releasing the coupling recess (18) in a radial guide (21) of the drive sleeve (7), which is biased into the coupling position by the force of a spring (34), a movement stop (23*a*) being associated with the coupling pin (19) which prevents the coupling pin (19) from falling out of the drive sleeve (7) when the tool (9) is withdrawn, the coupling recess (18) being formed to diverge radially outwardly and the coupling pin (19) at the coupling end thereof being formed to converge such that in the case of an overload on the tool (9) the coupling pin (19) is automatically displaced out of its coupling recess (18) against the force of the spring (34).

4. A handpiece (2,55) having a releasable mounting device, said device holding a medical tool (9), including a housing (3), a drive sleeve (7) mounted in said housing and which is mounted to be reciprocably displaceable in the longitudinal direction of a center axis (9*a*) and being selectively non-rotatable, rotatable and swingable around the center axis (9*a*) by a drive, or which is selectively mounted to be rotatable around the center axis (9*a*, 58) by a drive and axially non-displaceable in the housing (3, 56), and into which the tool (9) can be inserted with a shaft (11) thereof, a releasable coupling for connection of the shaft (11) with the drive sleeve (7), said tool shaft being engaged by said drive sleeve and being restrained from any radial movement a further releasable coupling for connection of the shaft (11)

with the drive sleeve (7) in the circumferential direction, a rotational position setting device (80) for the tool (9) being arranged between the drive sleeve and the shaft (11), all of said couplings being formed by a plurality of identical coupling recesses (18) in the shaft (11) evenly distributed around the circumference; coupling pins (19) being mounted to be radially moveable in radial guides (21) of the drive sleeve (7); a movement stop (23a) being associated with each coupling pin (19) which prevents the coupling pin (19) from falling out of the drive sleeve (7) when the tool (9) is withdrawn; and a mechanism which is manually accessible from the outside for shifting the coupling pin (19) from the coupling recess (18) into an uncoupling position.

5. A handpiece according to any one of claims 1 to 4, wherein a plurality of said coupling recesses (18) are distributed around the circumference of the shaft, said recesses being arranged in the same transverse plane.

6. A handpiece according to any one of claims 1 to 4, wherein the coupling pin (19) is rounded to form a ball shape at the coupling end.

7. A handpiece according to any one of claims 1 to 4, wherein the coupling pin (19) is mounted in a radial guide, comprising a radial guide hole (8) of the drive sleeve (7).

8. A handpiece according to claim 7, wherein the guide hole (8) is tapered in an internal edge region to a dimension which is smaller than the cross-sectional dimension of the coupling pin (19).

9. A handpiece according to any one of claims 1 to 4, wherein the radial dimension of the coupling pin (19) is larger than the radial thickness of the drive sleeve (7, 56a).

10. A handpiece according to any one of claims 1 to 4, wherein the coupling pin (19) and the drive sleeve (7) are displaceable by an axially displaceably mounted pressure member (27, 65), which pressure member acts with an inner oblique or conical surface (28) against the coupling pin (19) and is acted upon axially by the force of the spring.

11. A handpiece according to claim 10, wherein the pressure member (27) is directly manually accessible or accessible by means of an actuating element (29, 29a) from outside the housing (3), said actuating element (29, 29a, 62) being accessible from a side proximate to or remote from the tool, with which element the pressure member is displaceable against the force of the spring (34, 78) into a release position releasing the coupling pin (19).

12. A handpiece according to claim 11, wherein in the coupling position a gap is formed between the actuating element (29a, 72) and the pressure member (27, 65).

13. A handpiece according to any one of claims 1 to 4, wherein the handpiece has an angled head and the drive sleeve (7) is mounted in the angled head transversely of a longitudinal center axis (4) of the handpiece.

14. A handpiece according to claim 13, wherein the actuating element (29a) is formed by a push-button (31a) which is mounted displaceable longitudinally of the drive sleeve (7) on the side of the angled head distant from the tool in a guide (45) of the angled head housing or of a cover part (3a) and is biased by a spring (47) to the side distant from the tool (9).

15. A handpiece according to any one of claims 1 to 4, wherein the handpiece has a head (55) extending substantially straight, the drive sleeve (61) is arranged forwardly in the handpiece substantially coaxially and the tool (9) is insertable from the front into the drive sleeve (61).

16. A handpiece according to any one of claims 1 to 4, wherein the actuating element is mounted to be moveable parallel to the outer surface of the handpiece.

17. A handpiece according to claim 16, wherein the actuating element (63) is mounted to be pivotable around the longitudinal center axis (58) of the handpiece (55), and a drive (64) is arranged in the drive connection which converts a movement directed in the circumferential direction into an axial movement, and the actuating element (63) is formed by a rotatable ring or sleeve.

18. A handpiece according to claim 17, wherein the drive (64) has at least one carrying pin (72) radially penetrating the housing (56) of the handpiece (2), said carrying pin being arranged displaceably in a guide groove (73) in the wall of the housing (56) extending obliquely of the circumferential direction, said carrying pin protects radially outwardly and radially inwardly of a wall (56a) of the housing connection in a longitudinal guide with the actuating element (63) and with a radially inward end projects into a circumferential groove (75) of the pressure member (65).

19. A handpiece according to any one of claims 1 to 4, wherein each coupling recess (18) is bounded on a side thereof towards the tool by an edge (25).

20. A handpiece according to claim 19, wherein each edge (25) is formed by a ring groove (44), and each respective coupling recess (18) is arranged in the ring groove (44), whereby the effective depth of the coupling recess (18) is deeper than the effective depth of the ring groove (44).

21. A handpiece according to claim 19, wherein the coupling pin (19) and the edge (25) and the free end of the shaft (11) are configured by rounded or chamfered surfaces that upon respective insertion or upon removal of the shaft (11) into or out of the drive sleeve (7) the coupling pin (19) is displaced out of its coupling position.

22. A handpiece according to claim 19, wherein the coupling recess (18) is formed to diverge outwardly and the coupling pin (19) is formed to converge at the coupling end thereof.

23. A handpiece according to claim 19, wherein the coupling recess (18) has a hollow conically shaped, right angled or obtuse angled, cross-sectional form, whereby the obtuse conical angle (w1) is in the range of about 105° to 135°.

24. A handpiece according to claim 19, wherein the peripheral edges (18a) of the coupling recesses (18) which are adjacent each other in the circumferential direction have a spacing from one another or merge into one another with common peripheral edge sections (18b).

25. A handpiece according to claim 19, wherein there are provided eight coupling recesses (18) and coupling pins (19).

26. A handpiece according to claim 19, wherein at least the shaft (11) of the tool is constituted of a metal, such as steel or of a plastic material.

* * * * *